(12) United States Patent
Shin et al.

(10) Patent No.: US 8,440,148 B2
(45) Date of Patent: May 14, 2013

(54) MICROFLUIDIC DEVICE AND MICROFLUIDIC ANALYSIS EQUIPMENT

(75) Inventors: Dong-Ho Shin, Daejeon (KR); Minsuk Jeong, Jeongeup-si (KR); Kyu Ho Song, Seoul (KR); HyeYoon Kim, Daejeon (KR); JuHyun Jeon, Daejeon (KR); Moon Youn Jung, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 688 days.

(21) Appl. No.: 12/562,058

(22) Filed: Sep. 17, 2009

(65) Prior Publication Data

US 2010/0159574 A1    Jun. 24, 2010

(30) Foreign Application Priority Data

Dec. 23, 2008    (KR) .................. 10-2008-0131860

(51) Int. Cl.
*B01L 99/00*    (2010.01)
*G01N 21/01*    (2006.01)

(52) U.S. Cl.
USPC ........................... 422/504; 422/402; 422/412

(58) Field of Classification Search .......... 422/501–504, 422/402, 412, 507
See application file for complete search history.

(56) References Cited

U.S. PATENT DOCUMENTS

| 6,858,184 | B2 | 2/2005 | Pelrine et al. |
| 6,905,882 | B2 | 6/2005 | Buechler |
| 7,859,670 | B2 | 12/2010 | Kim et al. |
| 2008/0102006 | A1 | 5/2008 | Kram et al. |
| 2008/0112854 | A1 | 5/2008 | Park et al. |
| 2008/0135101 | A1 | 6/2008 | Lee et al. |
| 2009/0149345 | A1 | 6/2009 | Nishi et al. |

FOREIGN PATENT DOCUMENTS

| KR | 10-0773563 B1 | 11/2007 |
| KR | 10-2008-0074252 A | 8/2008 |
| KR | 10-0895228 B1 | 5/2009 |
| WO | WO 2004/105153 A2 | 12/2004 |

*Primary Examiner* — In Suk Bullock
*Assistant Examiner* — Paul Hyun

(57) ABSTRACT

Provided are a microfluidic device and a microfluidic analysis equipment. The microfluidic device includes guides disposed along both edges, a lower plate including a flow path defined between the guides, and a movable upper plate moved along the guides on the lower plate and having a length less than that the flow path. A fluid flow can be simply accurately controlled by adjusting a position of the movable upper plate. As a result, the fluid can sufficiently react in the detection part and the reaction part. Therefore, effective reaction and detection can be realized using only a small amount of fluid, thereby improving sensitivity. In addition, due to the improved sensitivity, a washing process for removing materials that are not consumed in the reaction can be omitted. Also, the movable upper plate can be manually moved using a user's finger.

20 Claims, 12 Drawing Sheets

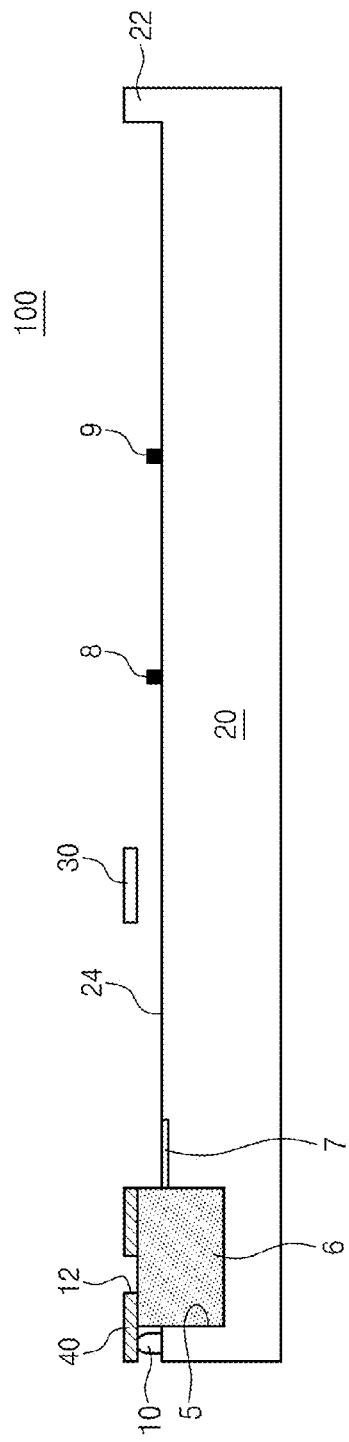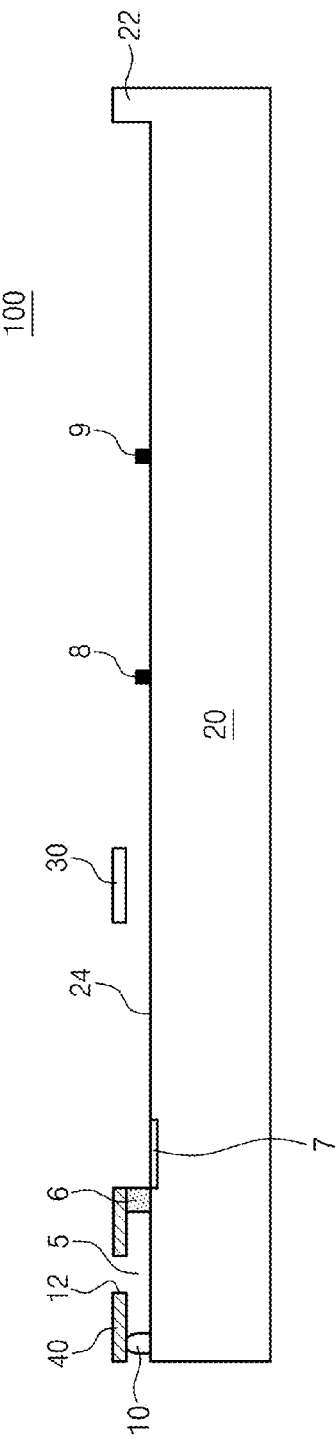

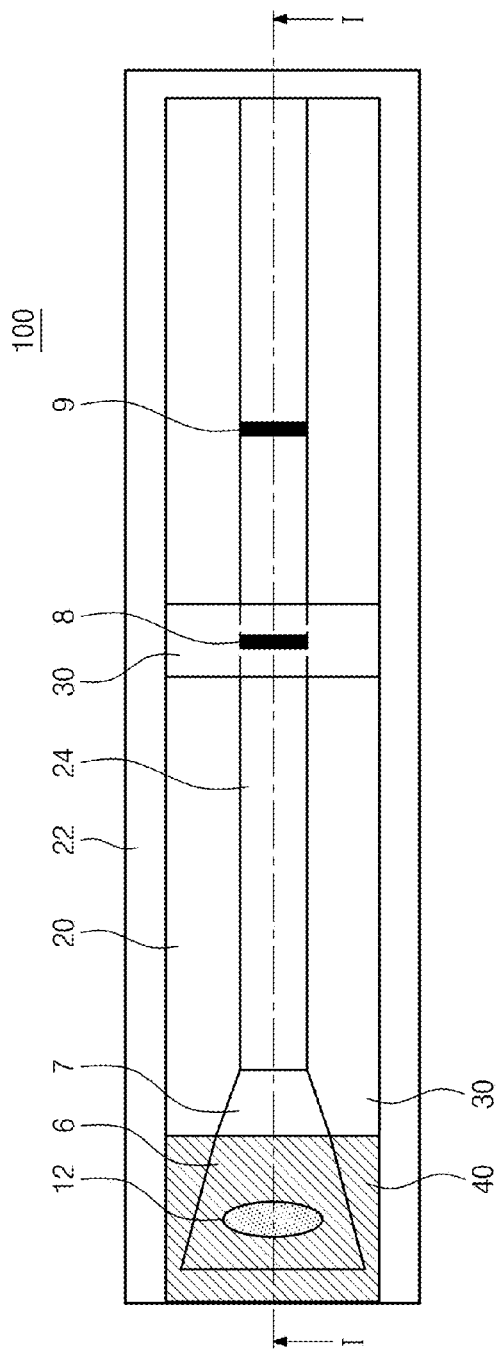
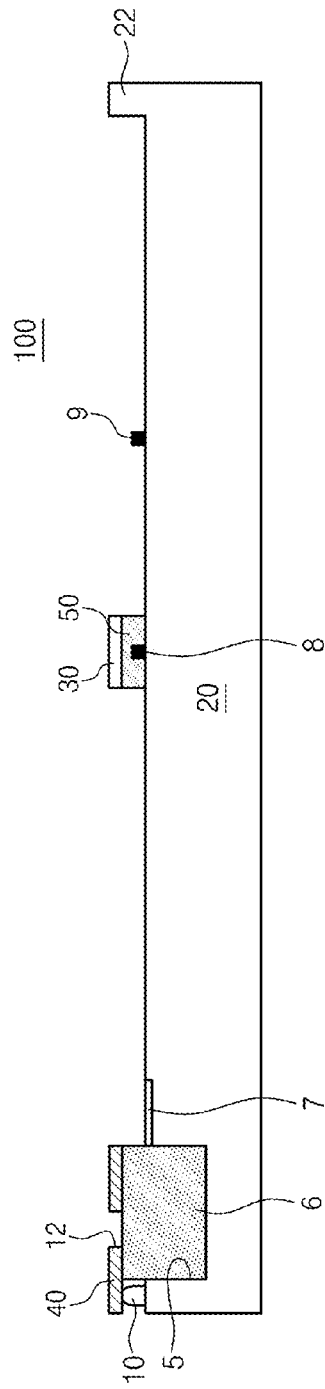
Fig. 5A
Fig. 5B

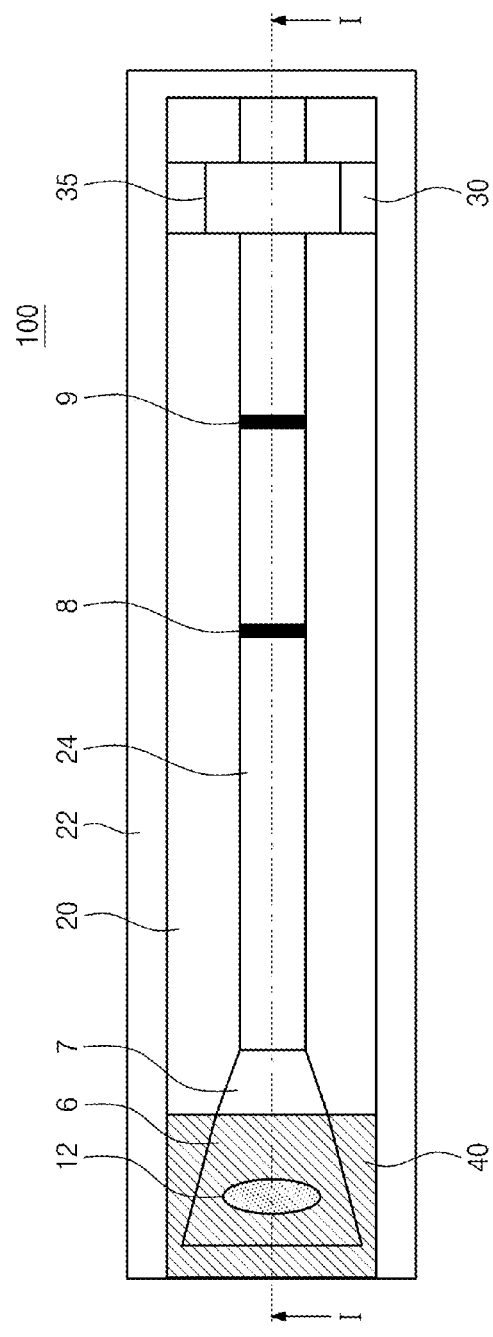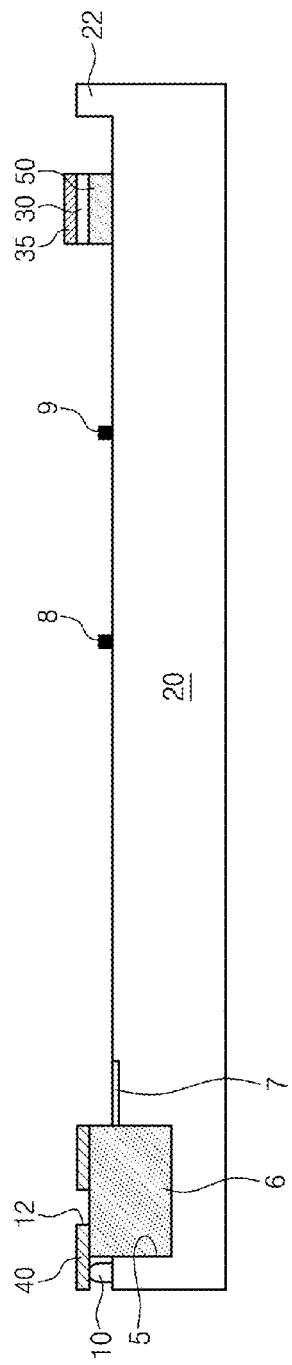

MICROFLUIDIC DEVICE AND MICROFLUIDIC ANALYSIS EQUIPMENT

CROSS-REFERENCE TO RELATED APPLICATIONS

This U.S. non-provisional patent application claims priority under 35 U.S.C. §119 of Korean Patent Application No. 10-2008-0131860, filed on Dec. 23, 2008, the entire contents of which are hereby incorporated by reference.

BACKGROUND OF THE INVENTION

The present invention disclosed herein relates to a microfluidic device and microfluidic analysis equipment.

Typical biochips quickly detect analytes such as biomaterials or environmental materials using membranes or hygroscopic papers. For example, biochips may be used for pregnancy diagnostic apparatuses, apparatuses for measuring hormones such as human chorionic gonadotropin (HCG), and alpha fetoprotein (AFP) (this is used as a liver cancer biomarker) measurements, which are currently commercialized. Biochips realized using membranes are disadvantageous for adjusting the flow of microfluid. The membranes may be formed of a polymeric material having a predetermined thickness and pores. Thus, the membranes are used for a simple test that determines whether an analyte is present at a previously set concentration or more. However, uniformity of sizes of the pores formed in the membranes is below the level required for an accurate test. In addition, if the sizes of the pores within the membrane are determined, strength of a capillary force is also determined. As a result, since it is impossible to adjust a microfluidic flow velocity in the membrane, the biochip realized using the membrane is not suitable for testing to accurately quantify the concentration of an analyte.

Alternatively, to overcome such limitations, there is a method which uses a microchannel as a passage for transferring a fluid. Based on hydrodynamics, a technology is widely used, which adjusts microfluidic flow velocity using microchannels with different widths and depths, and configurations of the microchannels are controlled to increase and decrease capillary force. There are many limitations in a typical biochip field in which a constant transfer velocity of the fluid in a microchannel, a constant reaction time in a reaction region, and a transfer stopping ability of fluid are necessary for quantifying analytes. Biochips using only capillary action are limited in that only the configuration and size of a channel are adjusted to accurately control fluid flow. Although a method in which an inner wall of the channel is surface-treated to have a hydrophilic property or a hydrophobic property to control the fluid was attempted, it is difficult to realize a biochip having a function that stops the fluid at a desired position and transfers the fluid to a desired position. For example, there is a technique in which a hydrophilic region of a capillary is defined to prevent the fluid from flowing so as to maintain constant reaction time. When the fluid reaches the hydrophilic region, the fluid flow is stopped due to a property in which the inner wall of the channel pushes the fluid. In general, most materials tend to have the hydrophilic property at the initial stage. However, if the materials contact the fluid for a long time, the materials tend to convert to the hydrophobic property. Thus, the fluid passes through the hydrophilic region at a very slow speed. During this time, the fluid is stopped in the channel in proportion to the surface area of the hydrophilic region. When the reaction time is controlled using such a method, a specific section of the channel should have the hydrophobic property. Thus, a suitable material and a processing method should be contrived in consideration of a physicochemical property of the fluid to be used. Also, in the case where the hydrophilic region of the channel is defined to prevent the fluid from flowing so as to maintain constant reaction time, there is a limitation that the hydrophilic property is insecure in the hydrophilic region due to absorption of atmospheric moisture, the amount of a reaction material, and inertial force of fluid flow in the reaction region. As a result, the reaction material within the reaction region may flow into the hydrophilic region.

There is a method in which pressure and electric energy are used to transfer and treat a fluid within a microfluidic device. In the case where pressure is used, a separate pressure regulator (e.g., a syringe pump or a peristaltic pump) is required, and the volume of a diagnosis system including a microfluidic device increases. In addition, the system price is affected by the pressure regulator more than the microfluidic device. Thus, this technique is unsuited for a point of care system (POCS) market in which a microfluidic device having a small size and a low price is required. On the other hand, it is advantageous that a relatively small system may be used in a method in which a fluid flow is controlled using an electrokinetic technique when compared to the method using pressure. However, a method for controlling the fluid using the electric energy may be used very limitedly. To apply the electric energy, an electrode should be provided in the microfluidic device. Accordingly, a unique configuration and method should be provided according to a property of the fluid, and various devices for transferring an electrical signal into the microfluidic device should be disposed in combination. Thus, it is complicated to manufacture and realize the system even if the system is small. Specifically, when many reaction processes are performed in one microfluidic device, the electric energy should be adjusted for each process in the case where the electrical property of the fluid is changed in each process. Therefore, the above-described method may be very complicated and difficult.

SUMMARY OF THE INVENTION

The present invention provides a microfluidic device that can simply and accurately control a fluid flow.

The present invention also provides a microfluidic device that can manually control a fluid flow.

The present invention also provides a microfluidic analysis equipment that can simply and accurately control a fluid flow to accurately analyze a fluid.

Embodiments of the present invention provide microfluidic devices including: a lower plate including a storage chamber in which a fluid is introduced, guides disposed along both edges, and a flow path disposed between the guides, having a height lower than upper ends of the guides, and connected to the storage chamber; an upper plate upwardly spaced a predetermined height apart from the storage chamber, the upper plate having a fluid injection hole through which the fluid is injected; a detection part disposed in a predetermined position of the flow path to detect a specific material contained in the fluid; and a movable upper plate moving along the guide and having a height equal to that of the upper plate and a length less than that the flow path. Here, the fluid may flow along the movable upper plate in a state where the fluid is in contact with a bottom surface of the movable upper plate, and a flow of the fluid may be controlled by a position of the movable upper plate.

In some embodiments, a bottom surface of the movable upper plate may be treated to have a property similar to that of the fluid. A surface of the flow path may be treated to have a property opposite to that of the fluid.

In other embodiments, the microfluidic devices may further include a guide rail groove defined in a predetermined region of an inner lateral surface of the guide. The movable upper plate may further include a lateral protrusion part inserted into the guide rail groove.

In still other embodiments, the microfluidic devices may further include a groove disposed between the guide and the flow path, the groove having a surface lower than that of the flow path.

In even other embodiments, the microfluidic devices may further include a reaction part disposed between the storage chamber and the detection part. The reaction part may be coated with a material reacting with a predetermined material contained in the fluid to generate a specific material detectable by the detection part. The upper plate may expose the reaction part.

In yet other embodiments, the microfluidic devices may further include a reaction part disposed between the storage chamber and the detection part. The reaction part may be coated with a material reacting with a predetermined material contained in the fluid to generate a specific material detectable by the detection part. The upper plate may extend to overlap with the reaction part.

In further embodiments, the fluid may include blood, a bottom surface of the movable upper plate may be treated to have a hydrophilic property, and a surface of the flow path may be treated to have a hydrophobic property. The microfluidic devices may further include a filter disposed in a predetermined region of the storage chamber.

In still further embodiments, the microfluidic devices may further include a movable upper plate fixing unit disposed on a top surface of the movable upper plate.

In other embodiments of the present invention, microfluidic analysis equipments include: a microfluidic device receiving part to which the microfluidic device is loaded; a fixed guide rail disposed on the microfluidic device receiving part; a movable upper plate catching part moved along the fixed guide rail, the movable upper plate catching part fixing a movable upper plate fixing unit; a position control part controlling a position of the movable upper plate catching part; a reading part reading a data value with respect to a specific material in a detection part of the microfluidic device; and an output part outputting the data value read by the reading part.

In some embodiments, the movable upper plate fixing unit may be formed of a magnetic material, and the movable upper plate catching part may include a magnet plate attached to the magnetic material.

In other embodiments, wherein the movable upper plate fixing unit may include an upper protrusion part protruding from a top surface of the movable upper plate, and the movable upper plate catching part may include a robot arm catching the upper protrusion part, a fixing groove in which the upper protrusion part is inserted, or an adhesive part adhering to a top surface of the upper protrusion part.

In still other embodiments, the microfluidic device may further include a lower plate electrode electrically connected to the detection part and disposed in a predetermined region of the lower plate, the microfluidic analysis equipment may further include a receiving part electrode disposed in a predetermined region of the microfluidic device receiving part, contacting with the lower plate electrode, and electrically connected to the reading part. Here, the reading part may read the data value with respect to the specific material in the detection part of the microfluidic device using an electrochemical method.

In even other embodiments, the microfluidic analysis equipments may further include an optical inspection part guide rail disposed over the receiving part; and an optical inspection part moved along the optical inspection part guide rail, electrically connected to the reading part and the position control part, and irradiating a laser onto a surface of the detection part to detect fluorescence emitted from the surface of the detection part. The reading part may read the data value with respect to the specific material in the detection part of the microfluidic device using a laser-induced fluorescence detection.

BRIEF DESCRIPTION OF THE FIGURES

The accompanying figures are included to provide a further understanding of the present invention, and are incorporated in and constitute a part of this specification. The drawings illustrate exemplary embodiments of the present invention and, together with the description, serve to explain principles of the present invention. In the figures:

FIG. 2A is a cross-sectional view taken along line I-I of FIG. 1 according to an embodiment of the present invention;

FIG. 2B is a cross-sectional view taken along line I-I of FIG. 1 according to another embodiment of the present invention;

FIGS. 4A, 5A, and 6A are views illustrating sequentially an operational state of a movable upper plate, which is moved together with a microfluid in a microfluidic device;

FIGS. 4B, 5B, and 6B are cross-sectional views taken along line I-I of FIG. 1, respectively;

FIG. 8A is a view illustrating an application example of FIG. 1;

FIG. 8B is a cross-sectional view taken along line I-I of FIG. 8A;

DETAILED DESCRIPTION OF PREFERRED EMBODIMENTS

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

Figure 1:
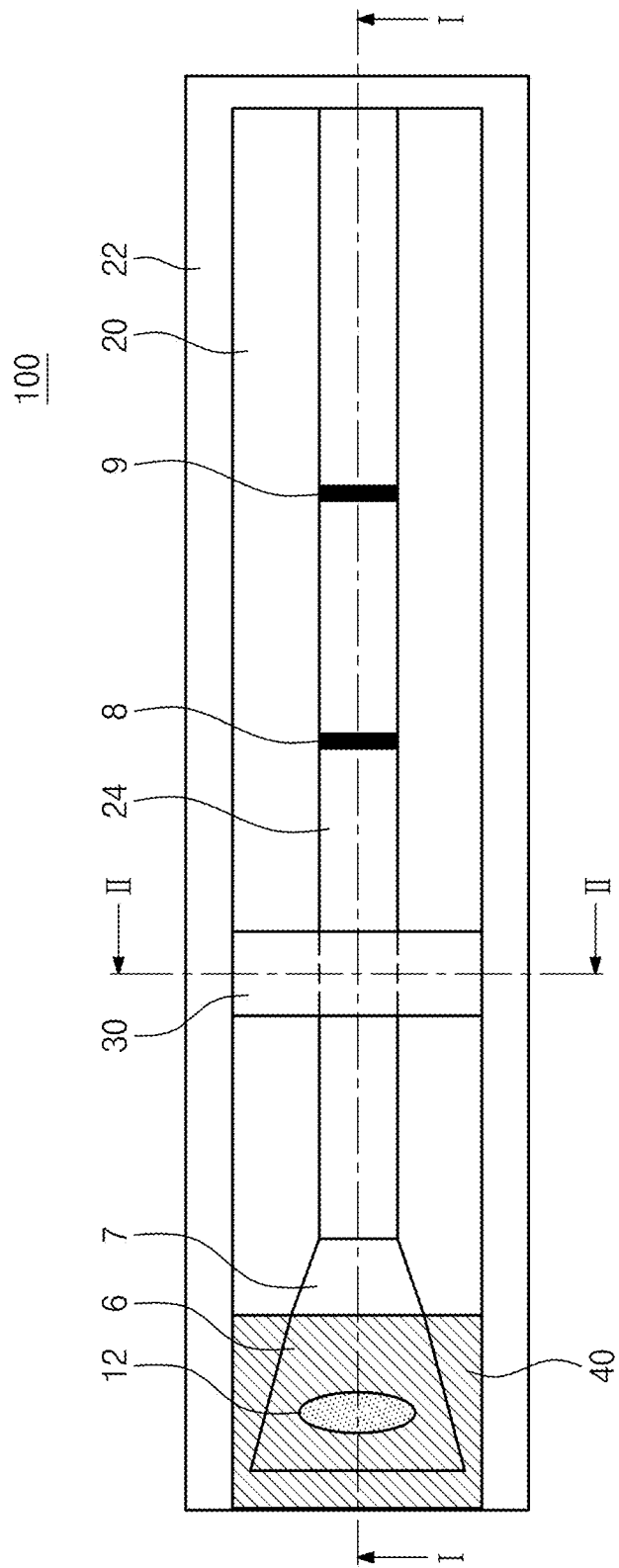
FIG. 1 is a plan view of a microfluidic device according to an embodiment of the present invention.
Figure 3:
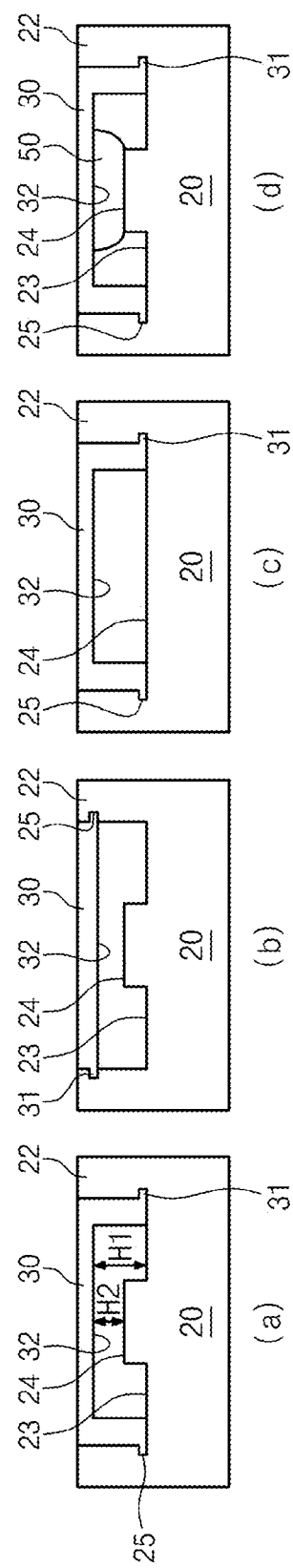
FIG. 3 is a cross-sectional view taken along line II-II of FIG. 1.

FIG. 1 is a plan view of a microfluidic device according to an embodiment of the present invention. FIG. 2A is a cross-sectional view taken along line I-I of FIG. 1 according to an embodiment of the present invention. FIG. 2B is a cross-sectional view taken along line I-I of FIG. 1 according to another embodiment of the present invention. FIG. 3 is a cross-sectional view taken along line II-II of FIG. 1.

Referring to FIGS. 1, 2A, 2B, and 3, a microfluidic device 100 according to this embodiment includes a lower plate 20 and an upper plate 40. The lower plate 20 includes a storage chamber 5 in which a fluid 50 is introduced, guides 22 disposed along both edges, and a flow path 24. The flow path 24 is disposed between the guides 22, has a height lower than upper ends of the guides 22, and is connected to the storage chamber 5. The upper plate 40 is upwardly spaced a predetermined height apart from the storage chamber 5 and has a fluid injection hole 12 through which the fluid 50 is injected. At least one or more detection parts 8 and 9 are disposed in predetermined positions of the flow path 24 to detect a specific material contained in the fluid 50. Although two detection parts 8 and 9 are illustrated in the drawings, the present invention is not limited thereto. This exemplarily illustrates that the two detection parts 8 and 9 detect two kinds of materials. For example, one detection part or two or more detection parts may be provided. The microfluidic device 100 is moved along the guides 22 and includes a movable upper plate 30 having a height equal to that of the upper plate 40 and a length less than that the flow path 24.

Referring to FIG. 3, a guide rail groove 25 is defined in a predetermined region inside the guide 22. The guide rail groove 25 may be defined at an inner lower portion of the guide 22 as illustrated in FIGS. 3(a) and 3(c) or may be defined at an inner upper portion of the guide 22 as illustrated in FIG. 3(b). The movable upper plate may have a "Π" shape in section as illustrated in FIG. 3(c) or may have a "—" shape in section as illustrated in FIG. 3(b). The movable upper plate 30 may further include a lateral protrusion part 31 inserted into the guide rail groove 25. As shown in FIGS. 3(a) and 3(b), a groove 23 having a bottom surface having a height lower than that of the flow path 24 may be further disposed between the flow path 24 and the guide 22. As a result, the flow path 24 may have an upwardly exposed top surface. Due to this structure, when the fluid 50 is transferred in a state where the fluid 50 is in contact with a bottom surface 32 of the movable upper plate 30, the fluid 50 exists on only an upper portion of the flow path 24 as illustrated in FIG. 3(d). As long as an additional force is not applied, the fluid 50 is not introduced into the groove 23 or does not leak from both lateral surfaces of the groove 23. A height difference H1 between the bottom surface 32 of the movable upper plate 30 and the bottom surface of the groove 23 and a height difference H2 between the bottom surface 32 of the movable upper plate 30 and a surface of the flow path 24 may be adjusted. The surface of the flow path 24 may be treated to be a property opposite to that of the fluid 50. The bottom surface 32 of the movable upper plate 30 may be treated to be a property similar to that of the fluid 50. For example, when the fluid 50 has a hydrophilic property, the surface of the flow path 24 may have a hydrophobic property, and the bottom surface 32 of the movable upper plate 30 may have a hydrophobic property. Also, similar to the surface of the flow path 24, an inner surface of the groove 23 may be treated to be a property opposite to that of the fluid 50. Due to the lower plate 20 and the structure and the surface treatment of the movable upper plate 30, the fluid 50 may be intended to be moved along the movable upper plate 30 having a greater surface tension, and thus, the fluid transfer may be easily and accurately controlled. The movable upper plate 30 may be manually moved using a user's finger, and may be freely moved in a direction desired by the user. As a result, the fluid 50 may be freely moved in a desired direction. In addition, it may prevent the fluid 50 from being lost during the fluid transfer.

For example, the fluid 50 may include blood. As shown in FIG. 2A, the storage chamber 5 may be disposed toward the inside of the lower plate 20 at a position lower than that of the bottom surface of the flow path 24. A filter 6 may be disposed inside the storage chamber 5. An upper surface of the filter 6 may be disposed at a position higher than that of a top surface of the flow path 24. As shown in FIG. 2B, the storage chamber 5 may have a bottom surface having a height equal to that of the bottom surface of the flow path 24. A filter 6 may be disposed between the storage chamber 5 and the flow path 24. When the fluid 50 is blood, the filter 6 may filter bulky materials such as a white blood corpuscle or a red blood corpuscle and pass only blood plasma (or a serum). A spacer 10 is disposed between an end of the upper plate 40 and an end of the lower plate 20 to prevent the fluid from flowing. A reaction part 7 may be disposed between the storage chamber 5 and the flow path 24. A material reacting with a certain material contained in the fluid 50 may be coated on the reaction part 7 to generate specific materials detectable by the detection parts 8 and 9.

Figure 4A:
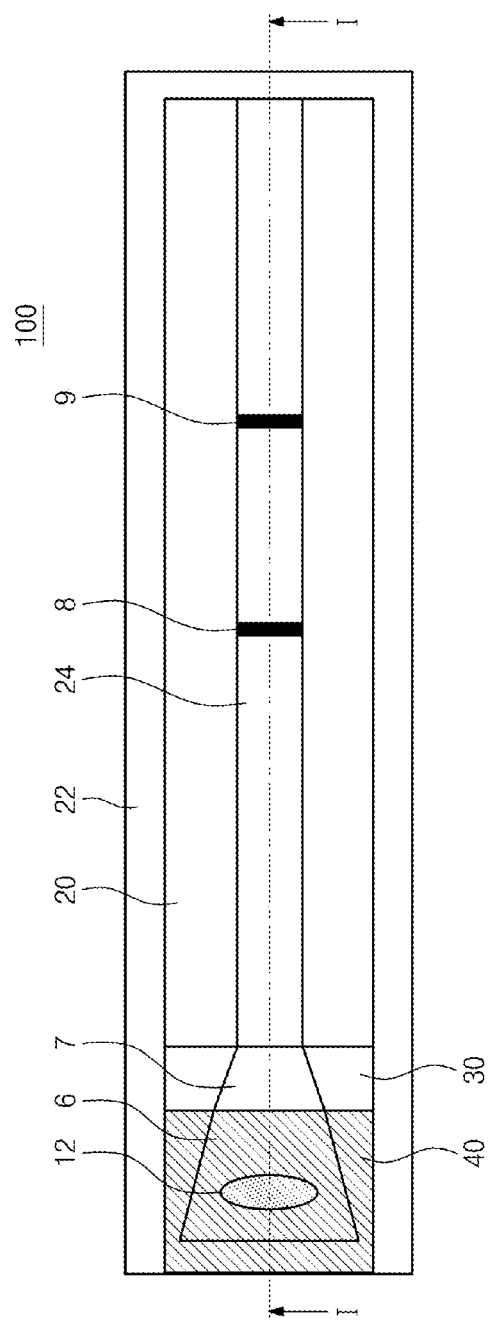
Figure 4B:
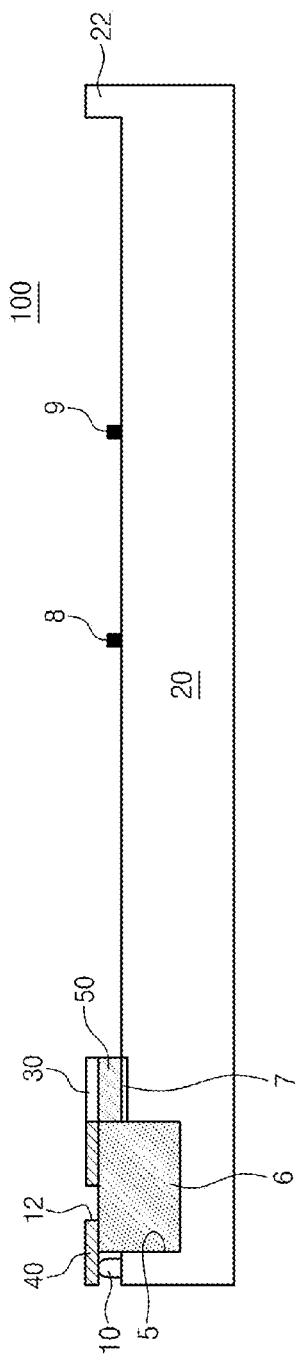
Figure 6A:
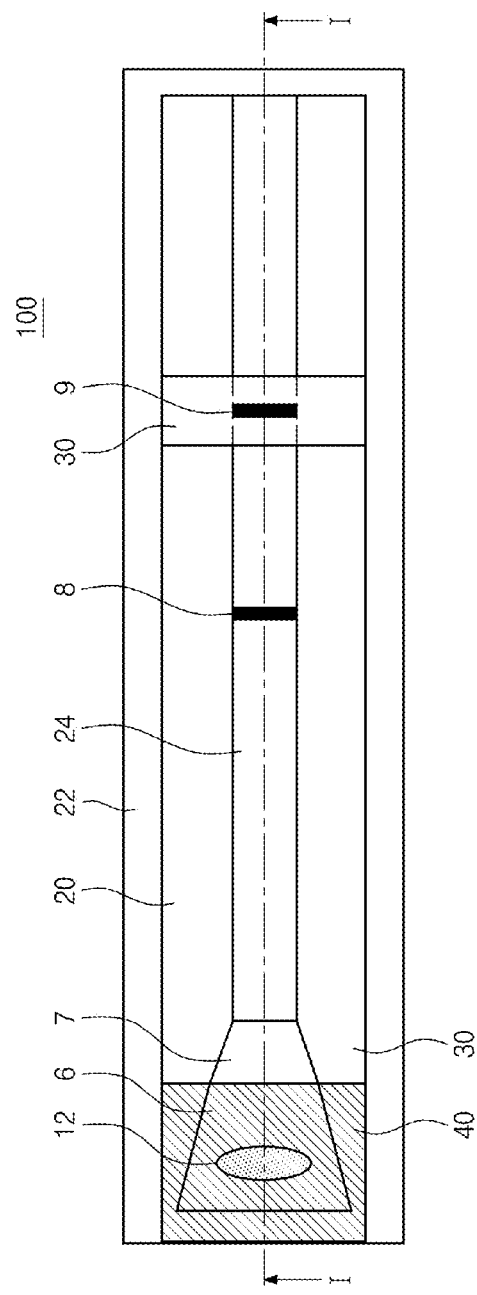
Figure 6B:
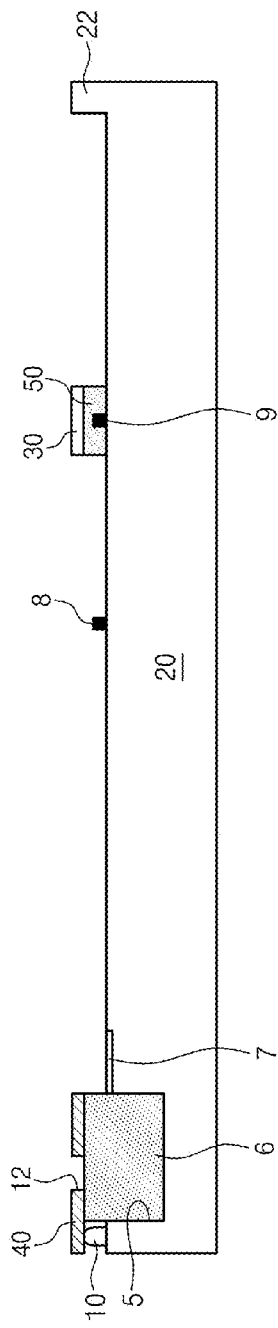

A method for utilizing a microfluidic device 100 as shown in FIGS. 1, 2A, and 3(a) will be described as an example with reference to FIG. 4A, 5A, and 6A and FIGS. 4B, 5B, and 6B that are cross-sectional views of FIGS. 4A, 5A, and 6A, respectively. FIGS. 4A, 5A, and 6A are views illustrating sequentially an operational state of a movable upper plate, which is moved together with a microfluid in a microfluidic device. FIGS. 4B, 5B, and 6B are cross-sectional views taken along line I-I of FIG. 1, respectively.

Referring to FIGS. 4A and 4B, a fluid 50 is injected through a fluid injection hole 12. The fluid 50 is filtered by a filter 6 within a storage chamber 5. When the fluid 50 is blood, bulky particles such as a white blood corpuscle or a red blood corpuscle are filtered by the filter 6, and only blood plasma (or a serum) passes through the filter 6. When a movable upper plate 30 is moved in a state of being contact with an upper plate 40, the fluid 50 passing through the filter 6 due to a capillary force is moved in a state of being contact with the movable upper plate 30. Since a reaction part 7 is in contact with the storage chamber 5, the movable upper plate 30 overlaps with the reaction part 7 at positions of the movable upper plate 30 of FIGS. 4A and 4B. Thus, the fluid 50 contacts with the reaction part 7. For example, a detection antibody may be coated on the reaction part 7 and may be fixed to a nanogold particle, a phosphor, or a fluorescent nanoparticle. A disease-specific antibody exists in the blood plasma. The disease-specific antibody contacts with the detection antibody coated on the reaction part 7 to cause a primary antigen-antibody reaction, thereby to generate a material in which a specific antigen is fixed to the detection antibody. In a state where the movable upper plate 30 is in contact with the upper plate 40, the fluid 50 is in contact with a bottom surface of the movable upper plate 30 and simultaneously in contact with the reaction part 7 disposed below the movable upper plate 30. Also, the fluid 50 does not flow into flow path 24 adjacent to the reaction part 7. This is done because an upper portion of the flow path 24 adjacent to the reaction part 7 is opened, and the fluid 50 is not affected by the capillary force.

When the primary antigen-antibody reaction is sufficiently completed, the movable upper plate 30 is slowly moved over an upper portion of a first detection part 8 as shown in FIGS. 5A and 5B. The movable upper plate 30 may be manually moved by a user's finger, or the microfluidic device 100 may be installed inside an analysis device to automatically move the movable upper plate 30. Since the movable upper plate 30 is moved, the fluid 50 is transferred also together with the movable upper plate 30. When the movable upper plate 30 is moved over the first detection part 8, the fluid 50 contacts with the first detection part 8. A capture antibody for capturing the detection antibody to which the nanogold particle or the fluorescent nanoparticle is fixed may be coated on the first detection part 8. Thus, an antigen-antibody reaction between the detection antibody bound to the antibody and the capture antibody starts in the first detection part 8 to generate a complex of a detection antibody-antigen-capture antibody.

When the antigen-antibody reaction is sufficiently completed in the first detection part 8, the movable upper plate 30 is slowly moved over an upper portion of a second detection part 9 as shown in FIGS. 6A and 6B. For example, the other capture antibody exists in the second detection part 9 to cause an antigen-antibody reaction, thereby to capture the complex of the detection antibody-antigen-capture antibody generated in the first detection part 8. When the antigen-antibody reaction is sufficiently completed, the movable upper plate 30 is moved. At this time, the complex of the detection antibody-antigen-capture antibody may be captured by the other capture antibody of the second detection part 9 and fixed to the second detection part 9. Thus, only materials that are not consumed in the reaction may be moved laterally along the movable upper plate 30.

Since fluid transfer may be easily and accurately controlled due to the structure and the surface treatment of the movable upper plate 30, the antigen-antibody reaction process may be performed using only a small amount of sample, and a washing process for removing the materials that are not consumed in the reaction may be omitted.

Figure 7A:
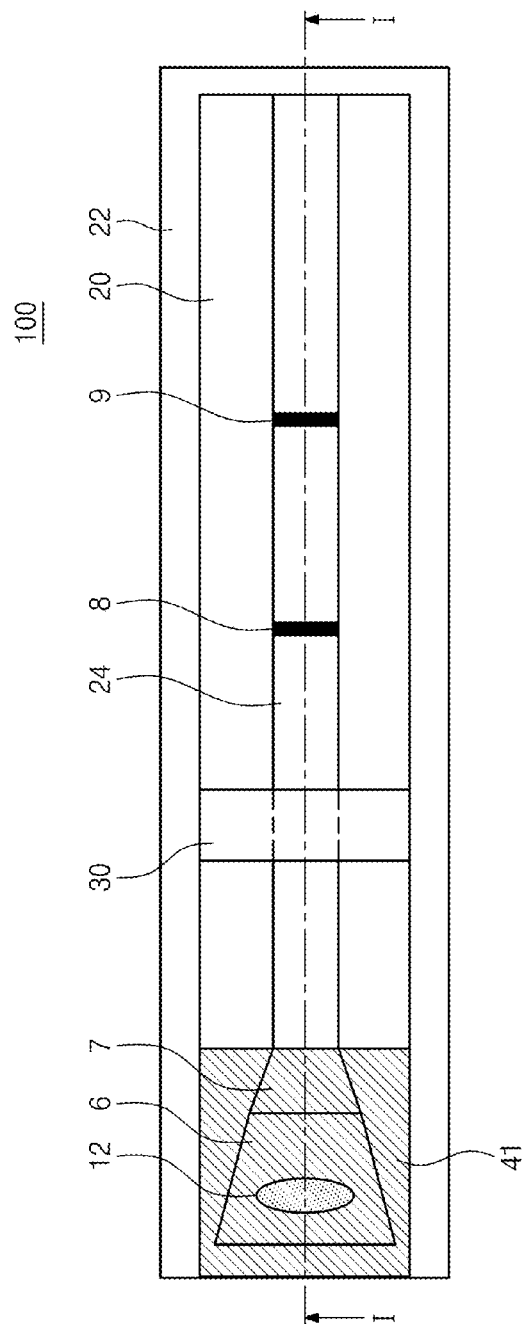
FIG. 7A is a plan view of a microfluidic device according to another embodiment of the present invention.
Figure 7B:
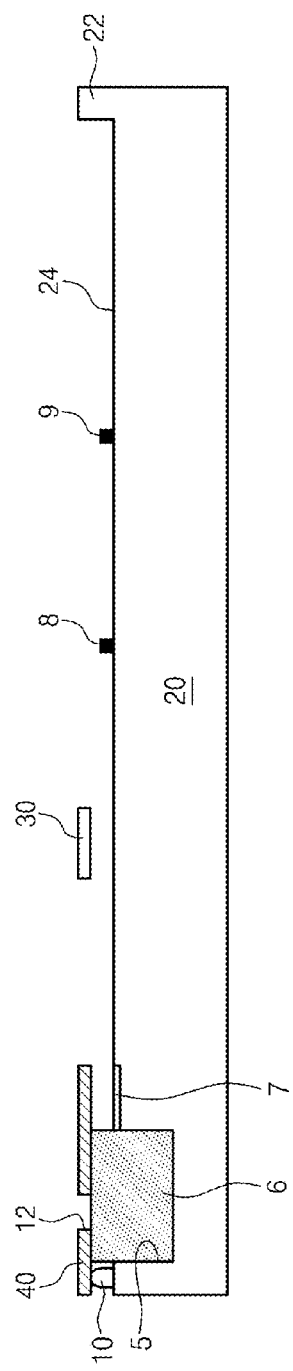
FIG. 7B is a cross-sectional view taken along line I-I of FIG. 7A.

The upper plate 40 may extend as shown in FIGS. 7A and 7B to overlap with the reaction part 7. In this case, the fluid 50 may be injected once to complete the reaction in the reaction part 7 even through the movable upper plate 30 does not contact with upper plate 40.

Although not shown, an electrode part electrically connected to the detection parts 8 and 9 and a display part and built-in softwares connected to the electrode part may be built in a lower part 20 of the microfluidic device 100. For example, the microfluidic device 100 may include a portable diagnostic lab-on-a-chip. In addition, a color may be expressed by the antigen-antibody reaction in the detection parts 8 and 9, like a pregnancy diagnostic apparatus.

An application example of a method in which a microfluidic device 100 is installed inside an analysis device such as a fluorescent scanner to automatically analyze an analyte without manually using (or operating) the microfluidic device 100 will be described below.

In this case, a fixing unit 35 adheres to a movable upper plate 30 as shown in FIGS. 8A and 8B. For example, the fixing unit 35 may be formed of a magnetic material or may include a metallic plate. The fixing unit 35 may be used as a unit for fixing the movable upper plate 30 as an example. The microfluidic device 100 may be conveyed inside microfluidic analysis equipments 200 and 300 illustrated in FIGS. 9 and 10.

Figure 9:
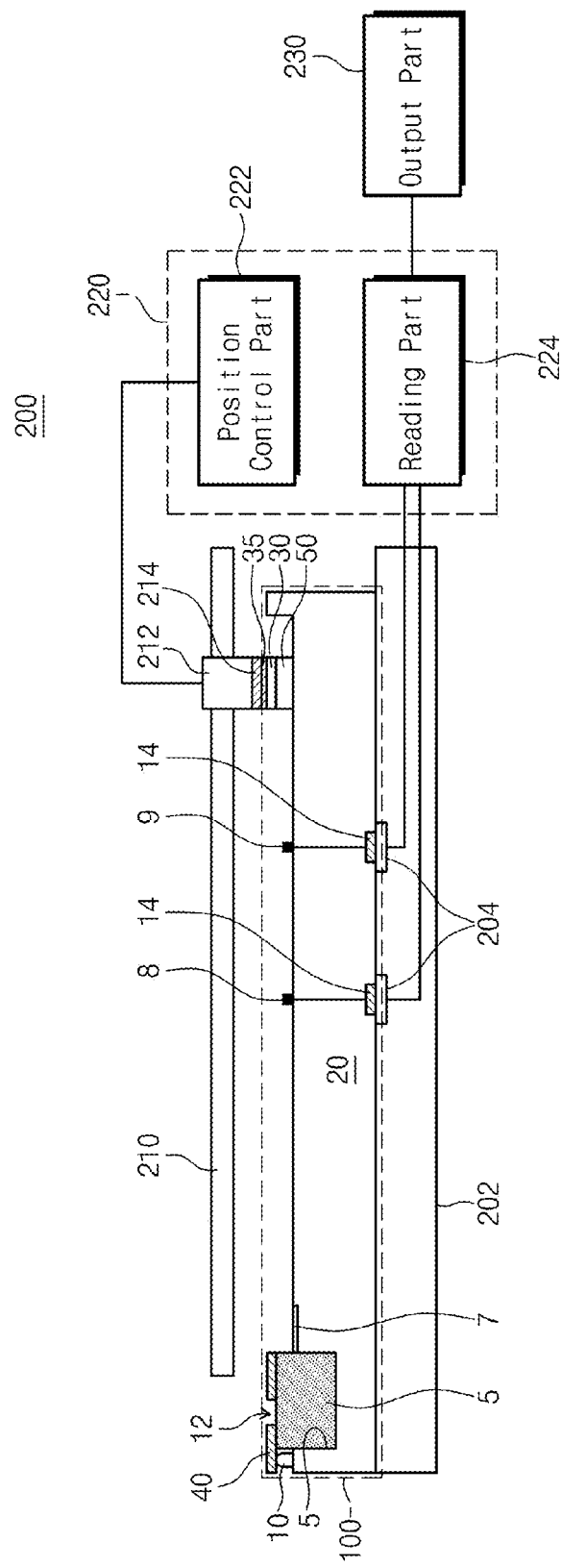
FIG. 9 is a view of a microfluidic detection device according to an embodiment of the present invention.

The microfluidic analysis equipment 200 of FIG. 9 detects and reads a specific material contained in a fluid using an electrochemical method.

In this case, a loaded microfluidic device 100 includes lower plate electrodes 14 electrically contacting with detection parts 8 and 9 in a lower plate 20 except for a fixing unit 35. A detection antibody to which a gold nanoparticle is fixed may be coated on a reaction part 7 of the microfluidic device 100, and a complex of a detection antibody-antigen-capture antibody to which the gold nanoparticle is fixed may be fixed to the detection parts 8 and 9. According to the electrochemical method, the specific material may be detected and read using a property in which conductivity increases due to the gold nanoparticle as the number of complex increases.

The microfluidic analysis equipment 200 may include a microfluidic device receiving part 202 in which the microfluidic device 100 is disposed. A receiving part electrode 204 contacting with the lower plate electrodes 14 may be disposed on the microfluidic device receiving part 202. The microfluidic analysis equipment 200 may include a fixed guide rail 210 disposed on the microfluidic device receiving part 202 and a movable upper plate catching part 212 moved along the fixed guide rail 210 and catching a fixing unit 35 of the movable upper plate 30. A magnet plate 214 attachable to the fixing unit 35 may be attached to a bottom surface of the movable upper plate catching part 212. In this case, the fixing unit 35 may be formed of a magnetic material. The microfluidic analysis equipment 200 may further include a central processing unit (CPU) 220. The CPU 220 may include a position control part 222 for controlling a position of the movable upper plate catching part 212 and a reading part 224 electrically connected to the receiving part electrode 204 to read a data value (e.g., such as conductivity) of a specific material detected by the detection parts 8 and 9. The data value read by the reading part 224 may be outputted by an output part 230.

A process for utilizing the microfluidic analysis equipment 200 will be described below.

A fluid 50 is dropped into a fluid injection hole 12, and the microfluidic device 100 is loaded on the microfluidic device receiving part 202 of the microfluidic analysis equipment 200. Then, the movable upper plate catching part 212 is moved along the fixed guide rail 210 by a signal of the position control part 222, disposed over the movable upper plate 30, and attached to the fixing unit 35 to fix the movable upper plate 30. The movable upper plate catching part 212 slowly moves the movable upper plate 30 onto the reaction part 7 and the detection parts 8 and 9 according to a program stored in the CPU 220. Then, the movable upper plate catching part 212 stops the movable upper plate 30 to induce the antibody-antigen reaction. When the complex of the detection antibody-antigen-capture antibody is sufficiently fixed in the detection parts 8 and 9 due to the antibody-antigen reaction, the reading part 224 reads a resultant data value to output the data value to the output part 230.

A process for detecting and reading a specific material within a fluid using a laser-induced fluorescence detection will be described with reference to FIG. 10.

In this case, a loaded microfluidic device 100 may not include the lower plate electrode 14 of FIG. 9. A detection antibody to which a fluorescent nanoparticle is fixed may be coated on a reaction part 7 of the microfluidic device 100, and a complex of a detection antibody-antigen-capture antibody to which the fluorescent nanoparticle is fixed may be fixed to detection parts 8 and 9. According to the laser-induced fluorescence detection, a laser is irradiated onto the detection parts 8 and 9 to which the complex is fixed to induce fluorescence of a phosphor. Also, the specific material may be detected and read using a property in which intensity of the fluorescence increases as the number of complex increases.

In the microfluidic analysis equipment 300, a receiving part 202 may not include a receiving part electrode 204. An optical inspection part guide rail 240 is disposed over the receiving part 202. An optical inspection part 250 is moved along the optical inspection part guide rail 240. The optical inspection part 250 may include an optical detection part 254 of a laser irradiation part 252. A position control part 222 may control a position of the optical inspection part 250. The optical detection part 254 is connected to a reading part 224, and a data value detected by the optical detection part 254 may be read by the reading part 224.

When a microfluidic device 100 in which a fluid 50 is dropped is loaded into the microfluidic analysis equipment 300, a movable upper plate catching part 212 slowly moves a movable upper plate 30 onto a reaction part 7 and detection parts 8 and 9 according to a program stored in a CPU 220. Then, the movable upper plate catching part 212 stops the movable upper plate 30 to induce an antibody-antigen reaction. When a complex of a detection antibody-antigen-capture antibody is sufficiently fixed in the detection parts 8 and 9 due to the antibody-antigen reaction, the optical inspection part 250 is moved over the detection parts 8 and 9 to irradiate a laser and detect fluorescence of a phosphor. The density of the fluorescence of the phosphor is read by the reading part 224 to output the resultant data value to the output part 230.

Figure 10:
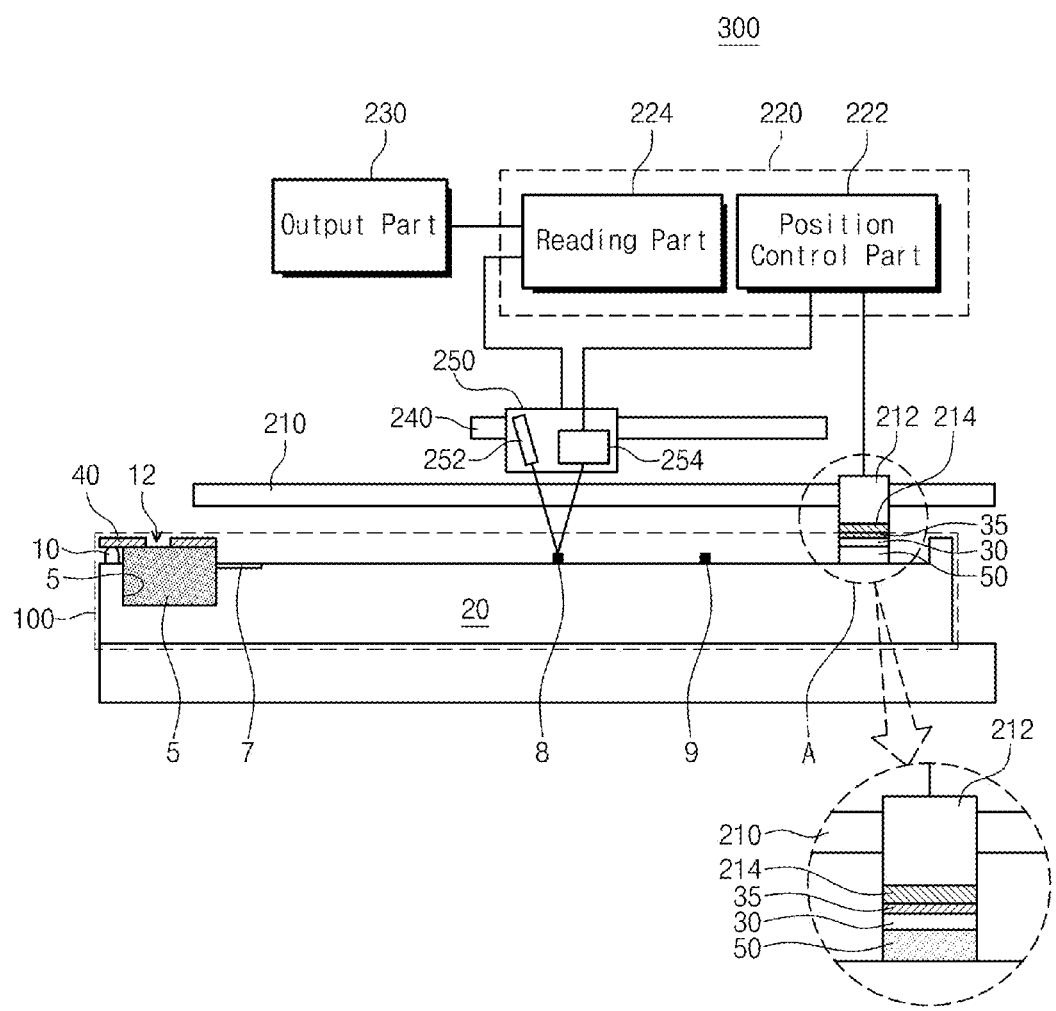
FIG. 10 is a view of a microfluidic detection device according to another embodiment of the present invention.

Although the movable upper plate catching part 212 is horizontally moved along fixed guide rail 210 in FIGS. 9 and 10, it will be apparent to those skilled in the art that the movable upper plate catching part 212 may be vertically moved by other components that are not shown in the drawings.

A modified example of a coupling relation between a movable upper plate catching part and a movable upper plate fixing unit will be described with reference to FIGS. 11A, 11B, and 11C.

Figure 11A:
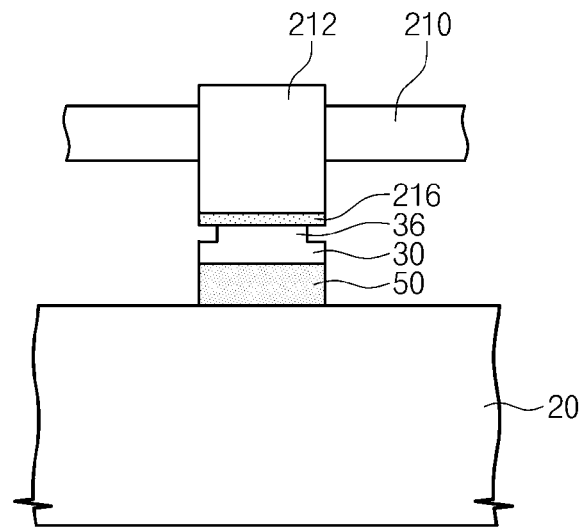
FIGS. 11A, 11B, and 11C are cross-sectional views illustrating a coupling relation between a movable upper plate catching part and a movable upper plate fixing unit, respectively.

Referring to FIG. 11A, a movable upper plate 30 may include an upper protrusion part 36 protruding upwardly from a fixing unit. The movable upper plate catching part 212 may include an adhesive part 216 adhering to a bottom surface thereof The adhesive part 216 may include an adhesive. Thus, since the adhesive part 216 adheres to a top surface of the upper protrusion part 36, the movable upper plate catching part 212 may be fixed.

Figure 11B:
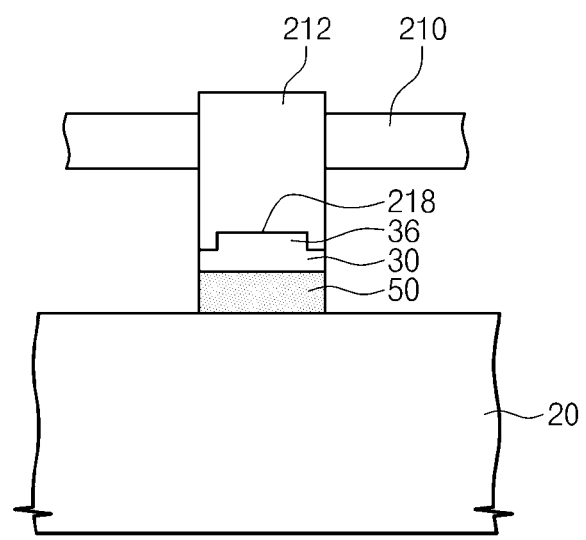

Referring to FIG. 11B, a fixing groove 218 engaged with the upper protrusion part 36 may be defined in the bottom surface of the movable upper plate catching part 212. Thus, since the fixing groove 218 is engaged with the upper protrusion part 36 of the movable upper plate 30, the movable upper plate 30 may be fixed.

Figure 11C:
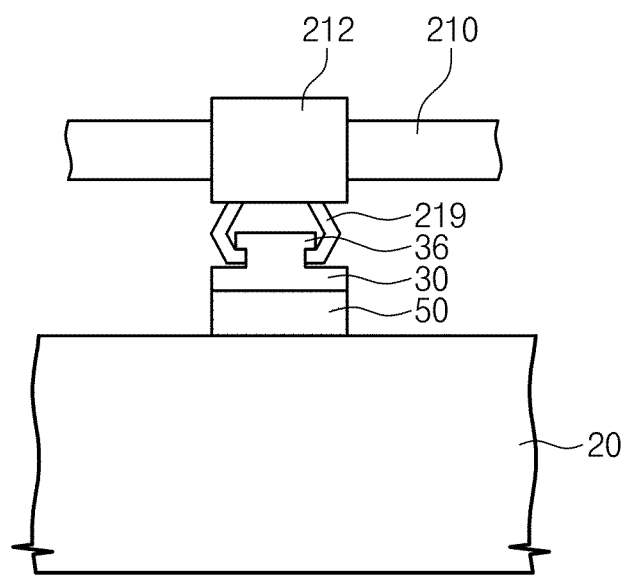

Referring to FIG. 11C, the movable upper plate catching part 212 may include a robot arm 219 for catching the upper protrusion part 36.

According to the microfluidic device of the embodiments, the movable upper plate can be adjusted in position to simply and accurately control the fluid flow. As a result, the fluid can sufficiently react in the detection part and the reaction part. That is, the reaction time of the fluid can be controlled according to the reaction system. Therefore, the effective reaction and detection can be realized using only a small amount of fluid, thereby improving sensitivity. In addition, due to the improved sensitivity, a washing process for removing the materials that are not consumed in the reaction can be omitted. Also, the movable upper plate can be manually moved using the user's finger.

Also, in the microfluidic analysis equipment according to the embodiments, the movable upper plate of the microfluidic device can be adjusted in position to simply and accurately control the fluid flow, thereby to accurately analyze the fluid.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A microfluidic device comprising:
   a lower plate comprising:
     a storage chamber configured to receive a fluid comprising a material of interest,
     first and second guides disposed along first and second edges of the lower plate respectively, wherein the first edge and the second edge face each other, and
     a flow path disposed between the first and the second guides, wherein a bottom surface of the flow path is located lower than an upper surface of any of the first and the second guides, and wherein the flow path abuts the storage chamber;
   an upper plate upwardly spaced from the storage chamber and having a fluid injection hole;
   a detection part disposed in the flow path and configured to detect the material of interest; and
   a movable upper plate configured to move along the first and the second guides, wherein the movable upper plate is spaced apart from the bottom surface of the flow path so that the received fluid can fill a space between the movable upper plate and the bottom surface of the flow path.

2. The microfluidic device of claim 1, wherein the movable upper plate is configured to capture the received fluid and move the captured fluid to a given location on the flow path.

3. The microfluidic device of claim 1, wherein the movable upper plate includes a hydrophilic or hydrophobic surface.

4. The microfluidic device of claim 3, wherein the flow path is configured to have wettability opposite to the wettability of the movable upper plate.

5. The microfluidic device of claim 1, the device further comprising first and second guide rail grooves formed in the first and the second guides, respectively,
   wherein the movable upper plate is coupled to the first and the second guides through the first and the second guide rail grooves, respectively.

6. The microfluidic device of claim 1, the device further comprising a groove disposed between any of the first and the second guides and the flow path,
   wherein the groove is located lower than the bottom surface of the flow path.

7. The microfluidic device of claim 1, the device further comprising a reaction part disposed between the storage chamber and the detection part,
   wherein the reaction part includes a reaction material, and
   wherein the upper plate is configured to expose the reaction part.

8. The microfluidic device of claim 1,
   wherein the device is configured to receive blood as a test sample,
   wherein the movable upper plate is configured to have a hydrophilic property,
   wherein the flow path is configured to have a hydrophobic property, and
   wherein the device further comprises a filter disposed between the storage chamber and the flow path.

9. The microfluidic device of claim 1, the device further comprising a movable upper plate fixing unit configured to stop the movable upper plate at a given location.

10. A microfluidic analysis equipment comprising:
    a microfluidic device receiving part into which the microfluidic device of claim 9 is loaded;

a fixed guide rail disposed over the microfluidic device receiving part;

a movable upper plate catching part configured to move along the fixed guide rail and fix the movable upper plate fixing unit;

a position control part configured to control a position of the movable upper plate catching part;

a reading part configured to read a data value upon detection of the material of interest by the detection part of the microfluidic device; and an output part configured to output the data value read by the reading part.

11. The microfluidic analysis equipment of claim 10, wherein
the movable upper plate fixing unit is formed of a magnetic material, and
wherein the movable upper plate catching part comprises a magnetic plate coupled to the magnetic material.

12. The microfluidic analysis equipment of claim 10, wherein
the movable upper plate fixing unit comprises an upper protrusion part protruding from a top surface of the movable upper plate, and
wherein the movable upper plate catching part comprises a robotic arm configured to catch the upper protrusion part, a fixing groove in which the upper protrusion part is inserted, or an adhesive part configured to adhere to a top surface of the upper protrusion part.

13. The microfluidic analysis equipment of claim 10,
wherein the microfluidic device further comprises a lower plate electrode electrically coupled to the detection part and disposed in a region of the lower plate,
wherein the microfluidic analysis equipment further comprises a receiving part electrode disposed in a predetermined region of the microfluidic device receiving part, in contact with the lower plate electrode, and electrically coupled to the reading part, and
wherein the reading part is configured to read the data value upon detection of the material of interest by the detection part of the microfluidic device using an electrochemical method.

14. The microfluidic analysis equipment of claim 10, the equipment further comprising an optical inspection part irradiating a laser onto a surface of the detection part to detect fluorescence emitted from the surface of the detection part,
wherein the reading part reads the data value upon detection of the material of interest by the detection part of the microfluidic device using laser-induced fluorescence detection.

15. The microfluidic analysis equipment of claim 14, further comprising an optical inspection part guide rail disposed over the microfluidic device receiving part,
wherein the optical inspection part is configured to move along the optical inspection part guide rail and is electrically coupled to the reading part and the position control part.

16. The microfluidic analysis equipment of claim 10, wherein the movable upper plate is configured to capture the received fluid and move the captured fluid to a given location on the flow path.

17. The microfluidic analysis equipment of claim 10, wherein the movable upper plate includes a hydrophilic or hydrophobic surface.

18. The microfluidic analysis equipment of claim 10, wherein the flow path is configured to have wettability opposite to the wettability of the movable upper plate.

19. The microfluidic analysis equipment of claim 10,
the microfluidic device further comprising first and second guide rail grooves formed in the first and the second guides, respectively,
wherein the movable upper plate is coupled to the first and the second guides through the first and the second guide rail grooves, respectively.

20. The microfluidic analysis equipment of claim 10, wherein the microfluidic device further comprises a groove disposed between any of the first and the second guides and the flow path, and
wherein the groove is located lower than the bottom surface of the flow path.

* * * * *